US011007237B2

(12) United States Patent
Obara et al.

(10) Patent No.: US 11,007,237 B2
(45) Date of Patent: May 18, 2021

(54) AGENT FOR SUPPRESSING CARBOHYDRATE BREAKDOWN AND ABSORPTION

(71) Applicant: KOHAKU BIO TECHNOLOGY CO., LTD., Tsukuba (JP)

(72) Inventors: Saya Obara, Tsukuba (JP); Reiko Takeda, Tsukuba (JP); Takuya Yamamoto, Tsukuba (JP); Norio Igarashi, Tsukuba (JP)

(73) Assignee: Kohaku Bio Technology Co., Ltd., Ibaraki (JP)

( * ) Notice: Subject to any disclaimer, the term of this patent is extended or adjusted under 35 U.S.C. 154(b) by 7 days.

(21) Appl. No.: 16/614,639

(22) PCT Filed: May 17, 2018

(86) PCT No.: PCT/JP2018/019914
§ 371 (c)(1),
(2) Date: Nov. 18, 2019

(87) PCT Pub. No.: WO2018/212362
PCT Pub. Date: Nov. 22, 2018

(65) Prior Publication Data
US 2020/0147160 A1 May 14, 2020

(30) Foreign Application Priority Data
May 19, 2017 (JP) .............................. JP2017-112066

(51) Int. Cl.
| A61K 36/00 | (2006.01) |
| A61K 36/15 | (2006.01) |
| A23L 33/10 | (2016.01) |
| A61P 3/08 | (2006.01) |
| A23L 2/52 | (2006.01) |

(52) U.S. Cl.
CPC ............... *A61K 36/15* (2013.01); *A23L 2/52* (2013.01); *A23L 33/10* (2016.08); *A61P 3/08* (2018.01); *A23V 2002/00* (2013.01)

(58) Field of Classification Search
CPC ..................................................... A61K 36/00
USPC ....................................................... 424/725
See application file for complete search history.

(56) References Cited

U.S. PATENT DOCUMENTS 7,887,858 B2 * 2/2011 Cauchard ............. A61K 8/9794
424/750

FOREIGN PATENT DOCUMENTS

| CN | 105596776 A | 5/2016 |
| JP | H06-62798 A | 3/1994 |
| JP | H09-227334 A | 9/1997 |
| JP | 2001-131048 A | 5/2001 |
| JP | 2004-083478 A | 3/2004 |
| JP | 2007-314522 A | 12/2007 |
| JP | 2008-189669 A | 8/2008 |
| JP | 2008-266260 A | 11/2008 |
| JP | 2010-235551 A | 10/2010 |
| JP | 2011-057556 | * 3/2011 |
| JP | 2011-057556 A | 3/2011 |
| JP | 2011-256164 A | 12/2011 |
| JP | 2012-201570 A | 10/2012 |
| JP | 2012-240967 A | 12/2012 |
| WO | 2006/030929 A1 | 3/2006 |
| WO | 2007/040006 A1 | 4/2007 |

OTHER PUBLICATIONS

"Chinese Medicine Basic Dictionary", Shanghai Science and Technology Publisher(Jiangsu New Medical School, Chinese Medicine Basic Dictionary, Editorial Department, edited by Shogakukan), vol. 2, pp. 860-862.
Deguchi et al., "Effects of Extract of Guava Leaves on the Development of Diabetes in the db/db Mouse and on the Postprandial Blood Glucose of Human Subjects", Journal of Japanese Agricultural Chemistry Society, vol. 72, No. 8, pp. 923-931, 1988 Japan.
Kobayashi et al., "Green Tea Polyphenols Inhibit the Sodium-Dependent Glucose Transporter of Intestinal Epithelial Cells by a Competitive Mechanism", J. Agric. Food Chem, 2000, 48, pp. 5618-5623 Japan.
Extended European search report dated Feb. 9, 2021 issued in the corresponding EP Patent Application No. 18802451.7.
Database WPI, Week 201202, Thomson Scientific, London, GB; AN 2011-Q64425, XP002801617 & JP 2011-256264 A (previously disclosed and submitted).
Database WPI, Week 200828, Thomson Scientific, London, GB; AN 2008-D91014, XP002801618, & JP 2007-314522 A (previously disclosed and submitted).
Database WPI, Week 201282, Thomson Scientific, London, GB; AN 2012-Q94821, XP002801619, & JP 2012-240967 A (previously disclosed and submitted).
Database WPI, Week 200901, Thomson Scientific, London, GB; AN 2009-A16482, XP002801620, & JP 2008-266260 A (previously disclosed and submitted).
Database Medline [Online], US National Library of Medicine (NLM), Bethesda, MD, US; 2001, Islas C A et al: "Structural characterisation of Baltic amber and its solvent extracts by several mass spectrometric methods.", XP002801621, Database accession No. NLM11382931 *abstract*.
Database WPI, Week 201202, Thomson Scientific, London, GB; AN 2011-Q64425, XP002801617 & JP 2011-256164 A (previously disclosed and submitted).

* cited by examiner

*Primary Examiner* — Michael V Meller
(74) *Attorney, Agent, or Firm* — Carrier Blackman & Associates, P.C.; Joseph P. Carrier; William D. Blackman

(57) ABSTRACT

The problem to be solved is to suppress an elevation of blood glucose level by suppressing decomposition and absorption of a carbohydrate in the body; and further prevent or improve diabetes and obesity derived from hyperglycemic symptoms and chronic hyperglycemia, for a long time. To attain the object, an agent for suppressing α-glucosidase activity and an agent for suppressing glucose absorption containing an amber extract as an active ingredient were invented.

1 Claim, 2 Drawing Sheets

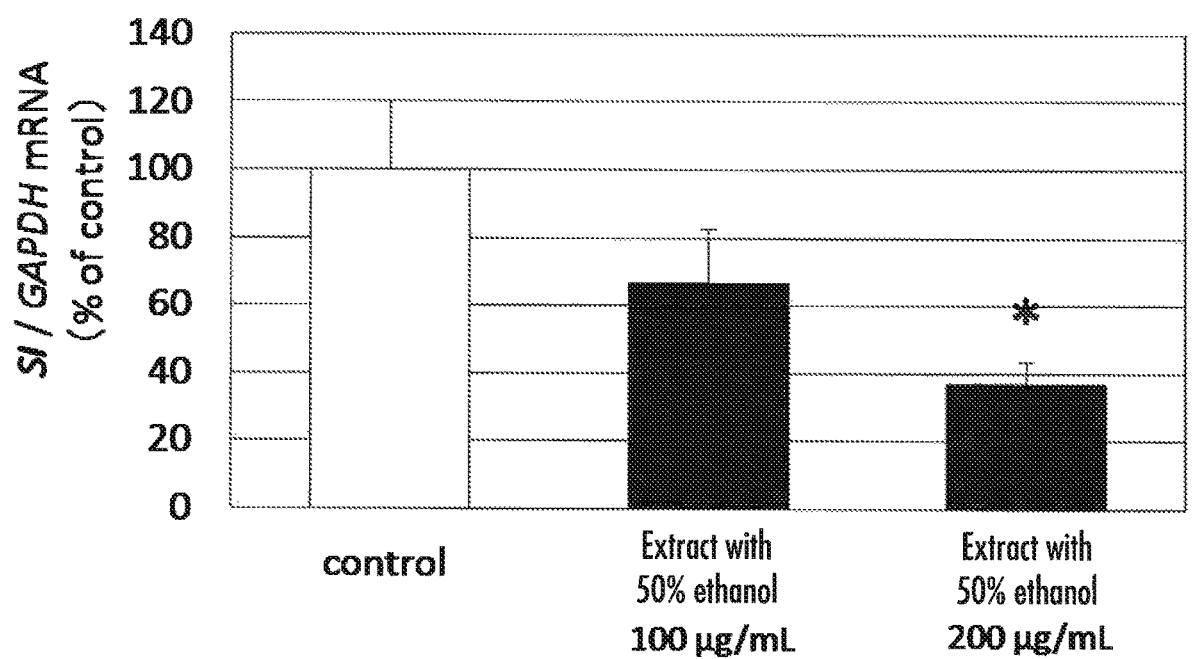

AGENT FOR SUPPRESSING CARBOHYDRATE BREAKDOWN AND ABSORPTION

TECHNICAL FIELD

The present invention relates to an agent for suppressing a-glucosidase activity and/or an agent for suppressing glucose absorption comprising an amber extract.

BACKGROUND ART

Amber is a fossil formed by lying a resin of principally a pine plant underground for a long time and condensing the resin. In China, a powder of amber has long been used as a Chinese medicine. Amber primarily contains a resin, an essential oil and succinic acid, and is slightly soluble in ethanol and diethyl ether or benzene (see, for example, Non Patent Literature 1).

Amber is well known as jewelry in Japan. Recently, powder and an extract of amber have been increasingly used in cosmetics and healthy foods. For example, a technique for blending amber power with a cosmetic to improve touch to the skin (see, for example, Patent Literature 1); a technique for blending an amber extract with an external preparation to skin (see, for example, Patent Literature 2 and Patent Literature 3); a technique for using the whitening effect of a hot-water extract of amber (see, for example, Patent Literature 4 and Patent Literature 5); a technique for using a skin turnover promoting factor contained in an amber extraction fraction (see, for example, Patent Literature 6); a technique for using a skin firming effect of an amber extract (see, for example, Patent Literature 7); a technique for using a hyaluronic acid production-promoting factor in an amber extraction fraction (see for example, Patent Literature 8); and a technique for using an angiogenesis-promoting factor contained in an amber extraction fraction (see, for example, Patent Literature 9) are known.

As described above, amber is known to have various physicochemical and biological effects and has been used in a wide variety of fields as an extremely useful material. Amber is expected as a material having unlimited potential.

In the meantime, diabetes, the number of patients of which has rapidly increased in these years, is a disease causing various metabolic abnormalities including chronic hyperglycemia. Type II diabetes, which occupies 90% or more of diabetes, is closely related to living practice and it is said that Type II diabetes can be prevented or mitigated by diet and exercise. Examples of the diabetic medicine that has been used include an incretin associated drug, a biguanide drug, a sulfonylurea drug, an insulin sensitizer, a thiazolidine drug and an a-glucosidase inhibitor. These drugs must be all used under supervision by a medical doctor and side effect is concerned in many cases. For these reasons, well daily control of blood glucose level by easy-to-take food and drink is desirable to prevent and improve diabetes. In the circumstance, development of a food material that can be added to a food and drink and has an action to suppress a postprandial elevation of blood glucose level, has been strongly desired.

A carbohydrate taken from meal is decomposed into monosaccharides such as glucose by a-glucosidase localized on the small intestine epithelium. The monosaccharides decomposed are taken by the small intestinal epithelial cells and transferred into the blood. Therefore, absorption of a carbohydrate contained in meal can be suppressed or delayed by suppressing the function of α-glucosidase and intake of glucose, with the result that a postprandial elevation of blood glucose level can be suppressed.

As a food material having an action to suppress an α-glucosidase activity, for example, a hot-water extract of guava leave (see, for example, Non Patent Literature 2) is known. As a food material having an action to suppress glucose absorption, for example, a tea polyphenol (see, for example, Non Patent Literature 3) is known. It is reported that succinic acid, which is known as a component contained in amber, showed an effect to suppress an elevation of blood glucose level in a rat diabetes model (see, for example, Patent Literature 10); however, the mechanism how to suppress has not been elucidated. It has not yet been reported that an amber extract has an effect to suppress an elevation of blood glucose level based on, e.g., an action to suppress α-glucosidase activity and an action to suppress absorption of glucose.

CITATION LIST

Patent Literatures

Patent Literature 1: Japanese Patent Laid-Open No. 2004-83478
Patent Literature 2: Japanese Patent Laid-Open No. H9-227334
Patent Literature 3: Japanese Patent Laid-Open No. 2001-131048
Patent Literature 4: Japanese Patent Laid-Open No. 2010-235551
Patent Literature 5: Japanese Patent Laid-Open No. 2012-240967
Patent Literature 6: Japanese Patent Laid-Open No. 2007-314522
Patent Literature 7: Japanese Patent Laid-Open No. 2008-189669
Patent Literature 8: Japanese Patent Laid-Open No. 2008-266260
Patent Literature 9: Japanese Patent Laid-Open No. 2011-256164
Patent Literature 10: Japanese Patent Laid-Open No. H6-62798

Non Patent Literatures

Non Patent Literature 1: Chinese Medicine Basic Dictionary, volume 2, Shanghai Science and Technology Publisher (Jiangsu New Medical School, "Chinese Medicine Basic Dictionary" Editorial Department, edited by Shogakukan)
Non Patent Literature 2: Yoriko Eguchi et al., Journal of Japanese Agricultural Chemistry Society, 72(8), 923-931 (1988)
Non Patent Literature 3: Y. Kobayashi, et al., J. Agric. Food. Chem., 48, 5618-5623 (2000)

SUMMARY OF INVENTION

Technical Problem

An object of the present invention is to provide an agent for suppressing α-glucosidase activity and/or an agent for suppressing glucose absorption that can be integrated into easy-to-take daily food and drink.

Solution to Problem

In consideration of the circumstance, the present inventors conducted intensive studies. As a result, they found that an amber extract has an effect to suppress α-glucosidase activity and/or an effect to suppress glucose absorption. Based on the finding, the present invention was achieved. The present invention is as follows.

<1> An agent for suppressing α-glucosidase activity comprising an amber extract.

<2> An agent for suppressing glucose absorption comprising an amber extract.

<3> The agent according to <1> or <2>, in which an extraction solvent for producing the amber extract is a hydroalcoholic solution (moisture content: 1 mass % to 60 mass %).

<4> An oral administration composition prepared by blending one or two or more of the agents according to any one of <1> to <3>.

<5> The oral administration composition according to <4>, wherein the aspect is a pharmaceutical product, a quasi-drug, a food and drink or a food additive.

Advantageous Effects of Invention

The present invention is an agent for suppressing α-glucosidase activity and/or an agent for suppressing glucose absorption comprising an amber extract. The agent for suppressing α-glucosidase activity and/or the agent for suppressing glucose absorption suppresses the activity of α-glucosidase localized on the small intestine epithelium to suppress decomposition of a carbohydrate and/or suppresses glucose absorption through the small intestinal epithelial cells to suppress/delay absorption of the carbohydrate. Accordingly, if the agent for suppressing α-glucosidase activity and/or the agent for suppressing glucose absorption is added to, e.g., a food and drink, absorption of a carbohydrate supplied by diet can be suppressed/delayed, thereby suppressing an elevation in blood glucose level; and further a food and drink useful for long-term prevention or improvement of diabetes and obesity derived from hyperglycemic symptoms and chronic hyperglycemia can be provided.

BRIEF DESCRIPTION OF DRAWINGS

FIG. 1 is a graph showing suppression of mRNA expression of a sucrase-isomaltase complex (hereinafter referred to as SI) by an amber extract in Caco-2 cells (n=3, *p<0.05, the term "50% ethanol extract" refers to the amber extract obtained in Production Example 1).

DESCRIPTION OF EMBODIMENTS

Amber Extract of the Present Invention

Figure 2A:
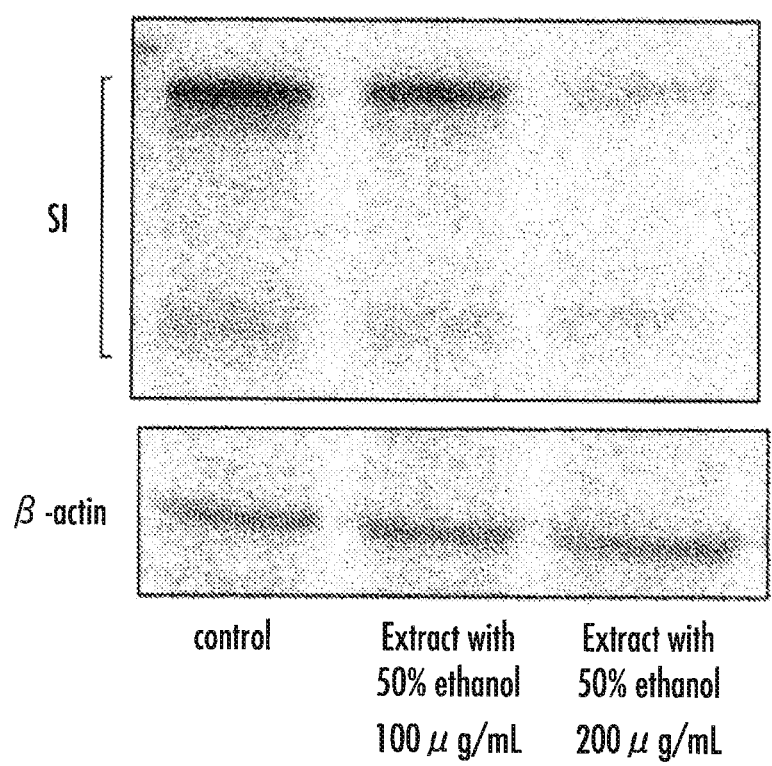
FIG. 2A shows an electropherogram and FIG. 2B shows a graph, both showing suppression of expression of a sucrase-isomaltase complex (SI) protein by an amber extract in Caco-2 cells (n=3, *p<0.05, **p<0.01, the term "50% ethanol extract" refers to an amber extract obtained in Production Example 1).

The agent for suppressing α-glucosidase activity and/or the agent for suppressing glucose absorption according to the present invention contains an amber extract as an active ingredient. The amber extract herein refers to, e.g., amber itself, processed amber such as crushed or chopped amber, an amber extract with a solvent added to amber or processed amber, a solvent-free amber extract obtained by removing the solvent from the amber extract, and purified products of these. Of them, an amber extract or a solvent-free amber extract is particularly preferable.

Examples of the solvent for the amber extract include water, an alcohol such as methanol, ethanol, 1,3-butanediol, propylene glycol and glycerin; an ester such as ethyl acetate and methyl formate; a nitrile such as acetonitrile; an ether such as diethyl ether and tetrahydrofuran; a halogenated hydrocarbon such as chloroform and methylene chloride; and a ketone such as acetone and methyl ethyl ketone. These solvents may be used singly or as a mixture (of two or more). Of these solvents, water or an alcohol is preferable and hydroalcoholic solution is more preferable. As the alcohol, ethanol is preferable. The content of water is preferably 1 mass % to 60 mass % and further preferably 10 mass % to 50 mass %. If the water content deviates from the upper or lower end of the range mentioned above, extraction efficiency may deteriorate.

An extraction method is as follows. For example, to crushed amber, a solvent in a volume 2 to 20 times of the amber is added. If the extraction is carried out at room temperature, the crushed amber may be soaked for several days; whereas, if the extraction is carried out at about the boiling point, the crushed amber may be soaked for several hours. Thereafter, the resultant extract is subjected to filtration to remove insoluble matter. The filtrate may be concentrated under vacuum. The concentrate may be purified by column chromatography using a column packed with silica gel, octadecylsilyl silica gel or ion exchange resin.

Production Example 1

Amber powder (100 g) was extracted with 50% ethanol (ethanol having water content of 50%). The extract was concentrated under vacuum and lyophilized to obtain 10 g of a 50% ethanol extract.

The extract obtained can be examined for action to suppress α-glucosidase activity, for example, by the following method. The extract is added to human colon cancer-derived cells (hereinafter referred to as Caco-2 cells) and the cells are cultured. The cultured cells are collected. With a crude enzyme solution thereof, sucrose or maltose serving as substrate is allowed to react. The amount of glucose generated is quantified by an enzyme method using glucose oxidase. An action to inhibit glucose uptake can be examined by the following method. To Caco-2 cells differentiated into the intestinal epithelial-like, glucose and the extract were simultaneously added. The amount of glucose taken in the cells or permeated through the cells is quantified by an enzyme method using glucose oxidase.

Examples of drinks containing the extract of the present invention include tea drinks, coffee drinks, soft drinks, alcohol drinks, milk drink, carbonated drinks, healthy drinks, nutrition drinks, sports drinks and concentrated stock solutions of these and preparation powders. Examples of food include gums, candies, jellies, tablets, healthy food, nutritional supplementary food and supplements.

When the extract of the present invention is used as a medicine such as a prophylactic agent for diabetes, the extract is provided in the dosage form of a powder, a granule, a tablet, a capsule, a liquid and an injection. The extract of the present invention can be orally administered directly or as a dilution of the extract with water. Alternatively, the extract of the present invention may be prepared into a preparation in combination with a pharmaceutical carrier known in the art. More specifically, the extract of the present invention can be administered as an oral liquid preparation such as a syrup or as an oral solid preparation, such as tablets, capsules, granules and powders, which is prepared by processing the extract of the present invention into a liquid extract or a powder and blending the liquid extract or power with a pharmaceutically acceptable carrier. As the pharmaceutically acceptable carrier, an organic or inorganic carrier substance ordinarily used as preparation material is used and blended as an excipient, a lubricant, a binder and a disintegrant in a solid preparation, and as a solvent, an excipient, a suspending agent and a binder in a liquid preparation. If necessary, additives such as a preservative, an antioxidant, a coloring and a sweetener can be used in the preparations.

In a food and drink or a pharmaceutical composition containing the extract of the present invention, the extract of the present invention can be added in any concentration. The extract of the present invention is preferably added in a concentration of 1 to 100 µg/ml and more preferably in a concentration of 5 to 50 µg/ml.

The effective dosage can be appropriately determined depending on the age and body weight of a patient, the type and severity of the disease, and the administration route.

EXAMPLES

Now, the present invention will be more specifically described by way of Examples below; however, the present invention is not limited to these Examples.

Example 1: Suppression Test for Sucrase/Maltase Activity

The test herein was carried out with reference to the method of OGAWA et al. (N. Ogawa et al., the Journal of Nutrition, 130: 507-513, 2000).

To Dulbecco's modified eagle medium (DMEM)(manufactured by Thermo Fisher Scientific K.K.), 10% fetal bovine serum (hereinafter referred to as FBS)(manufactured by Thermo Fisher Scientific K.K.), a 1% antibacterial agent (Penicillin-Streptomycin-L-Glutamine) (manufactured by FUJIFILM Wako Pure Chemical Corporation) and a 1% non-essential amino acid mixture (MEM Non-Essential Amino Acids) (manufactured by Thermo Fisher Scientific K.K.) were added to prepare a culture solution (hereinafter referred to as DMEM culture medium). In the DMEM culture solution (medium), Caco-2 cells were suspended. The suspension was added in 24-well plates (manufactured by TPP) in a ratio of $1.0 \times 10^4$ cells/cm$^2$ to seed the cells. The cells were cultured under 95% air/5% carbon dioxide gas at 37° C. for 8 to 10 days until the cultured cells reached confluency while exchanging the medium at intervals of 2 to 3 days. After the culture supernatant was removed by suction, the amber extract (50% ethanol extract) obtained in Production Example 1 was dissolved in dimethyl sulfoxide (hereinafter referred to as DMSO) so as to obtain a final concentration of 100 and 200 µg/mL. The DMSO solutions were mixed with DMEM culture medium (DMSO final concentration: 0.25%) and each added in an amount of 500 µL. DMSO was added to DMEM culture medium so as to obtain a DMSO final concentration of 0.25% and treated. This was used as a control. Acarbose (hereinafter referred to as ACA) was dissolved in DMSO so as to obtain a final concentration of 100 µg/mL, added to a DMEM culture medium (DMSO final concentration:0.25%) and treated. This was used as a positive control. In addition, the suppression test for sucrase/maltase activity was carried out by using succinic acid in the corresponding amount to that contained in amber extract. More specifically, the content of succinic acid in the amber extract obtained in Production Example 1 was calculated by analysis/preparative high performance liquid chromatographic apparatus and a Fourier transform infrared spectrophotometer. As a result, it was confirmed that the content rate of succinic acid is 2% or less. Then, succinic acid was dissolved in DMSO such that a final concentration was 2, 5 and 25 µg/mL and then added to a DMEM culture medium (DMSO final concentration: 0.25%) and treated. These plates were cultured under 95% air-5% carbon dioxide gas at 37° C. for 7 days.

Cells were collected with a lysis buffer (0.1 M phosphate buffer (pH6.8), 0.5% TritonX-100), allowed to stand still on ice for 20 minutes and centrifuged (10,000×g) at 4° C. for 30 minutes, and then, the supernatant was collected. A sucrose solution (sucrose dissolved in PBS (+), concentration: 56 mM) or a maltose solution (maltose dissolved in PBS (+), concentration: 56 mM) was added in an amount equivalent to the supernatant, mixed and allowed to react at 37° C. for one hour. Thereafter, the amount of the glucose generated was quantified in accordance with an enzyme method using glucose CII test Wako (manufactured by FUJIFILM Wako Pure Chemical Corporation). The sucrase activity and maltase activity were calculated, respectively, based on the production amount of glucose. Then, the enzyme activity of the control sample is regarded as 100 and the relative changes for the samples containing a test substance were calculated.

Table 1 shows the measurement results of sucrase and maltase activity. The amber extract of the present invention exhibits strong action to suppress sucrase activity and maltase activity in Caco-2 cells. In contrast, effects to suppress the sucrase activity and maltase activity were not confirmed in Caco-2 cells treated with the corresponding amount of succinic acid to that contained in the amber extract. In short, the amber extract of the present invention contains a component suppressing sucrase activity and maltase activity in Caco-2 cells, and the component was found to be a compound other than succinic acid or a mixture thereof.

TABLE 1

| Sample | Sucrase activity (%) (n = 3) | Maltase activity (%) (n = 3) |
| --- | --- | --- |
| Control | 100.0 ± 2.7 | 100.0 ± 3.5 |
| ACA: 100 µg/mL | 90.2 ± 4.1 | 39.4 ± 2.1*** |
| Amber extract of Production Example 1: 100 µg/mL | 61.8 ± 2.0*** | 71.0 ± 0.9* |
| Amber extract of Production Example 1: 200 µg/mL | 37.5 ± 1.7*** | 33.8 ± 1.7*** |
| Succinic acid: 2 µg/mL | 102.3 ± 3.0 | 108.3 ± 1.5 |
| Succinic acid: 5 µg/mL | 95.4 ± 1.4 | 99.2 ± 1.3 |
| Succinic acid: 25 µg/mL | 99.2 ± 2.0 | 100.9 ± 2.1 |

*$p < 0.05$,
***$p < 0.001$

Example 2: Suppression Test for mRNA Expression of Sucrase-Isomaltase Complex

In DMEM culture medium, Caco-2 cells were suspended. The suspension was added in dishes (manufactured by TPP) having 4 cm in diameter in a ratio of $1.0 \times 10^4$ cells/cm$^2$ to seed the cells. The cells were cultured under 95% air-5% carbon dioxide gas at 37° C. for 10 days until the cultured cells reached confluency while exchanging the medium at intervals of 2 to 3 days. After the culture supernatant was removed by suction, the amber extract obtained in Production Example 1 was dissolved in DMSO so as to obtain a final concentration of 100 and 200 µg/mL. The DMSO solutions were mixed with a DMEM culture medium (DMSO final concentration:0.25%) and each was added in an amount of 1 mL. DMSO was added to DMEM culture medium so as to obtain a DMSO final concentration of 0.25% and treated. This was used as a control. These dishes were cultured carried out under 95% air-5% carbon dioxide gas at 37° C. for 7 days.

Total RNA (hereinafter referred to as total RNA) was extracted from the cells treated, by use of RNA purification kit NucleoSpin RNA (manufactured by MACHEREY-NA-GEL). The amount of total RNA was obtained based on absorbance measured by a nanoscale spectrophotometer (Nano 200) at 260 nm. Subsequently, the total RNA was subjected to an RT reaction using PrimeScript™ RT reagent Kit (manufactured by Takara Bio Inc.) in accordance with the protocol attached to the kit. Using SYBR (trademark) Premix Ex Taq™ II (manufactured by Takara Bio Inc.) and in accordance with the protocol attached to the Premix, a reaction solution was prepared. The reaction solution was allowed to react with a sucrase-isomaltase complex (hereinafter referred to as SI) and individual primers of an internal standard, GAPDH (manufactured by Thermo Fisher Scientific K.K.) in accordance with a quantitative RT-PCR method. The expression level of SImRNA of a control sample was regarded as 100 and the relative changes for the samples containing a test substance were calculated. The values obtained at this time were corrected based on the value of GAPDH serving as the internal standard.

The results of SI mRNA expression are shown in FIG. 1. It was confirmed that the amber extract of the present invention suppresses SI mRNA expression.

Example 3: Suppression Test for SI Protein Expression

In DMEM culture medium, Caco-2 cells were suspended. The suspension was added in dishes (manufactured by TPP) having 4 cm in diameter in a ratio of $1.0 \times 10^4$ cells/cm² to seed the cells. The cells were cultured under 95% air-5% carbon dioxide gas at 37° C. for 10 days until the cultured cells reached confluency while exchanging the medium at intervals of 2 to 3 days. After the culture supernatant was removed by suction, the amber extract obtained in Production Example 1 was dissolved in DMSO so as to obtain a final concentration of 100 and 200 μg/mL. The DMSO solutions were mixed with a DMEM culture medium (DMSO final concentration: 0.25%) and each was added in an amount of 1 mL. DMSO was added to DMEM culture medium so as to obtain a DMSO final concentration of 0.25% and treated. This was used as a control. These dishes were subjected to culture carried out under 95% air-5% carbon dioxide gas at 37° C. for 8 days.

The cells were collected with RIPA Buffer (manufactured by Precision Castparts Corp.) and centrifuged (10,000×g) at 4° C. for 15 minutes. The supernatant was collected. The amount of the total protein was obtained based on absorbance at 595 nm by use of Bradford reagent (manufactured by Bio-Rad Laboratories, Inc.). Then, polyacrylamide electrophoresis was carried out in accordance with a routine method and proteins were transferred onto a polyvinylidene difluoride membrane (manufactured by Bio-Rad Laboratories, Inc.). SI protein was detected by using a mouse anti-human SI (A-12) antibody (manufactured by Santa Cruz Biotechnology, Inc.) as a primary antibody and a goat horseradish peroxidase-labeled anti-mouse antibody (manufactured by Santa Cruz Biotechnology, Inc.) as a secondary antibody. Internal standard, β-actin protein, was detected by using a rabbit anti-human β-actin antibody (manufactured by Abcam plc.) as a primary antibody and a donkey horseradish peroxidase-labeled anti-rabbit antibody (manufactured by Jackson ImmunoResearch Inc.) as a secondary antibody. Bands were detected by reacting ECL (manufactured by Bio-Rad Laboratories, Inc.) with a secondary antibody and detecting a signal by a chemiluminescence detection-specific imaging device. Analysis was carried out by use of Image J software. The SI protein expression level of a control sample was regarded as 100 and the relative changes for the samples containing a test substance were calculated. The values obtained at this time were corrected based on the value of internal standard, β-actin.

Figure 2B:
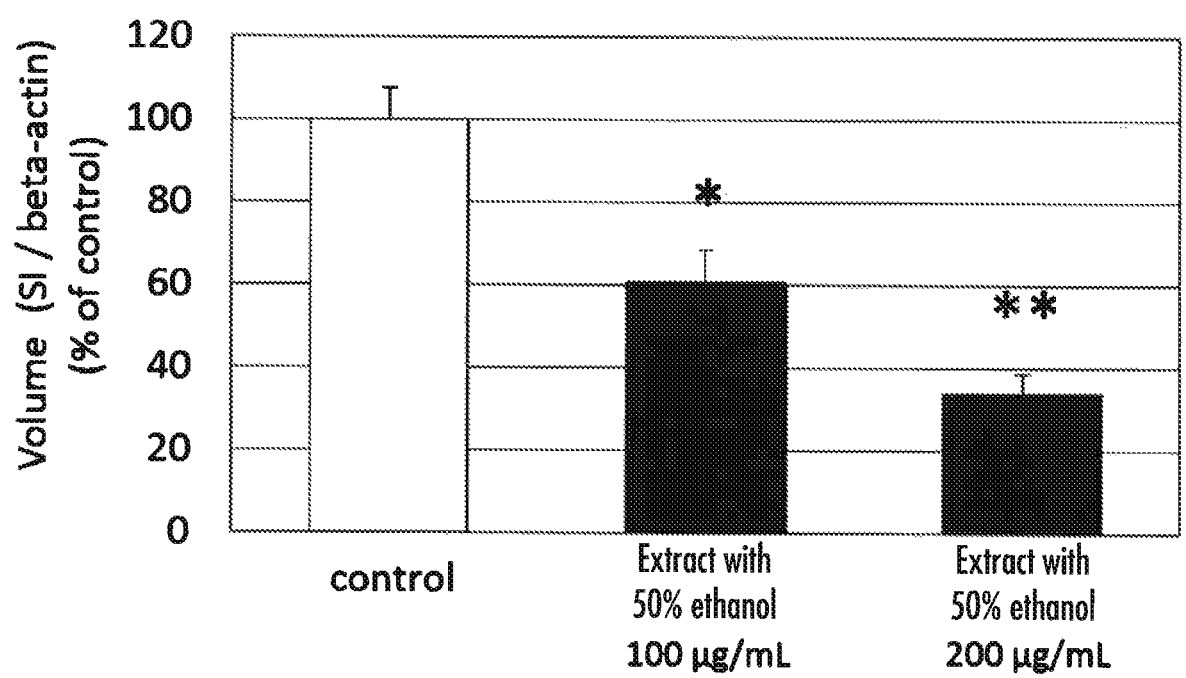

The results of SI protein expression are shown in FIG. 2. FIG. 2(a) shows a representative example of bands of western blot. The average values of integrated signal intensity values (Volume) of bands were calculated and are shown in FIG. 2(b). It was confirmed that the amber extract of the present invention suppresses SI protein expression.

Example 4: Suppression Test for Glucose Uptake by the Intestinal Epithelial-Like Cells (Caco-2 Cells)

The test herein was carried out in accordance with the method of Konishi et al. (Konishi et al., Biosci. Biotechnol. Biochem., 67(4), 856-862, 2003). In DMEM culture medium, Caco-2 cells were suspended. The suspension was added in Transwell-COL of 12 mm diameter and 0.4 μm in pore size (manufactured by Corning Incorporated) (hereinafter referred to as Transwell) in a ratio of $1.0 \times 10^5$ cells/cm² to seed the cells. The cells were cultured under 95% air-5% carbon dioxide gas at 37° C. for 3 weeks while exchanging the medium at intervals of 2 to 3 days.

After an intercellular electrical resistance (TER value) was confirmed to be 350 Ω·cm² or more by Millicell ERS-2 resistance measurement system (manufactured by Merck Millipore), the amber extract obtained in Production Example 1 was dissolved in DMSO on the apical side so as to obtain a final concentration of 0.2, 1 and 2 mg/mL, and mixed with a solution obtained by dissolving D(+)-glucose in PBS (+) in a concentration of 0.5% (hereinafter referred to as the 0.5% glucose solution) (DMSO final concentration: 1%). The resultant mixed solutions each were added in an amount of 500 μL. DMSO was added to a 0.5% glucose solution so as to obtain a DMSO final concentration of 1% and treated. This was used as a control. Phlorizin n-hydrate derived from an apple (hereinafter referred to as phlorizin) was dissolved in DMSO so as to obtain a final concentration of 1 mg/mL and mixed with the 0.5% glucose solution. The resultant DMSO solution (DMSO final concentration: 1%) was treated and used as a positive control. Further, succinic acid was subjected to a glucose permeation suppression test in the amount corresponding to that contained in the amber extract. More specifically, the content of succinic acid in the amber extract obtained in Production Example 1 was calculated by use of analysis/preparative high performance liquid chromatographic apparatus and Fourier transform infrared spectrophotometer. As a result, the content rate of succinic acid was confirmed to be 2% or less. Then, succinic acid was dissolved in DMSO so as to obtain a final concentration of 0.02, 0.05 and 0.1 mg/mL and mixed with PBS (+)(DMSO final concentration: 1%) and treated. At each basolateral side, 500 μL of PBS (+) was added. These transwells were subjected to culture carried out under 95% air −5% carbon dioxide gas at 37° C. for 2 hours. Thereafter the amount of glucose permeated on the basolateral side was quantified by use of glucose CII test Wako. The glucose permeability of the control sample was regarded as 100 and the relative changes for the samples containing a test substance were calculated. After the test, the TER value was confirmed to be 350 Ω·cm² or more.

The results of glucose permeability are shown in Table 2. It was found that the extract of the present invention suppresses uptake of glucose by the intestinal epithelial-like cells (Caco-2 cells). In contrast, in Caco-2 cells treated with the corresponding amount of succinic acid to that contained in the amber extract, glucose permeation suppression effect was not confirmed. In other words, the amber extract of the present invention contains a component suppressing permeation of glucose in the Caco-2 cells and the component is found to be a compound other than succinic acid or a mixture thereof.

TABLE 2

| Sample | Glucose permeability (%) (n = 3) |
| --- | --- |
| Control | 100.0 ± 3.8 |
| Phlorizin: 1 mg/mL | 27.4 ± 1.8*** |
| Amber extract of Production Example 1: 0.2 mg/mL | 72.9 ± 5.3* |
| Amber extract of Production Example 1: 1 mg/mL | 46.6 ± 1.2** |
| Amber extract of Production Example 1: 2 mg/mL | 37.4 ± 3.1*** |
| Succinic acid: 0.02 mg/mL | 94.6 ± 1.6 |
| Succinic acid: 0.05 mg/mL | 92.8 ± 3.2 |
| Succinic acid: 0.1 mg/mL | 95.4 ± 2.5 |

*$p < 0.05$,
**$p < 0.01$,
***$p < 0.001$

The invention claimed is:

1. A tablet or capsule consisting essentially of a *Pinus succinifera* extract, a solvent selected from the group consisting of ethyl acetate, methyl formate, acetonitrile, diethyl ether, tetrahydrofuran, chloroform, methylene chloride, acetone, and methyl ethyl ketone; and Dimethyl sulfoxide.

* * * * *